US012758120B2

(12) United States Patent
Lychagov et al.

(10) Patent No.: US 12,758,120 B2
(45) Date of Patent: Oct. 13, 2026

(54) DEVICE FOR METABOLISM MONITORING BY MEANS OF MOS SENSOR AND A CORRESPONDING METHOD

(71) Applicant: Samsung Electronics Co., Ltd., Suwon-si (KR)

(72) Inventors: Vladislav Valerievich Lychagov, Saratov (RU); Arthur Amirovich Mannanov, Chelyabinsk (RU); Artem Andreevich Dolgoborodov, Arkhangelsk (RU); Kirill Gennadievich Belyaev, Saint-Petersburg (RU); Jangpyo Park, Suwon-si (KR); Yongwon Jeong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 648 days.

(21) Appl. No.: 17/994,800

(22) Filed: Nov. 28, 2022

(65) Prior Publication Data

US 2023/0128963 A1 Apr. 27, 2023

Related U.S. Application Data

(63) Continuation of application No. PCT/KR2022/016035, filed on Oct. 20, 2022.

(30) Foreign Application Priority Data

Oct. 22, 2021 (RU) ................................ 2021130936

(51) Int. Cl.

| | |
|---|---|
| ***A61B 5/083*** | (2006.01) |
| ***A61B 5/00*** | (2006.01) |
| ***A61B 5/097*** | (2006.01) |

(52) U.S. Cl.

CPC .......... *A61B 5/0836* (2013.01); *A61B 5/0833* (2013.01); *A61B 5/097* (2013.01);

(Continued)

(58) Field of Classification Search

CPC ..... A61B 5/083; A61B 5/0836; A61B 5/0833; A61B 5/097

See application file for complete search history.

(56) References Cited

U.S. PATENT DOCUMENTS 5,178,155 A * 1/1993 Mault .................... A61B 5/083 600/538

6,712,770 B2 3/2004 Lin et al.

(Continued)

FOREIGN PATENT DOCUMENTS

KR 10-1947254 B1 2/2019

WO 2007/089328 A2 8/2007

(Continued)

OTHER PUBLICATIONS

Das et al., Non-Invasive Monitoring of Human Health by Exhaled Breath Analysis: A Comprehensive Review, Journal of the Electrochemical Society, 167, 2020 (Year: 2020).*

(Continued)

*Primary Examiner* — Puya Agahi

(74) *Attorney, Agent, or Firm* — Jefferson IP Law, LLP

(57) ABSTRACT

A device and a method for metabolism monitoring of a user based on low-cost, energy-effective and ultra-compact metal-oxide semiconductor (MOS) sensor are provided. The device provides information on metabolism/nutrition/physical activity of the user based on measuring the MOS sensor resistance proportional to a ratio of oxygen (O2) to carbon dioxide (CO2) concentrations in exhaled air.

19 Claims, 8 Drawing Sheets

(52) U.S. Cl.
CPC .......... *A61B 5/7264* (2013.01); *A61B 5/7278* (2013.01); *A61B 2562/029* (2013.01)

(56) References Cited

U.S. PATENT DOCUMENTS

| | | | | |
|---|---|---|---|---|
| 7,108,659 | B2 | 9/2006 | Ross et al. | |
| 10,078,074 | B2 | 9/2018 | Tsow et al. | |
| 10,143,401 | B2 | 12/2018 | Tao et al. | |
| 10,271,766 | B1 | 4/2019 | Parker, Jr. et al. | |
| 11,375,950 | B2 | 7/2022 | Meirav | |
| 2004/0186390 | A1* | 9/2004 | Ross | A61B 5/083 600/532 |
| 2005/0228239 | A1* | 10/2005 | Shallenberger | A61K 31/56 600/300 |
| 2009/0227887 | A1 | 9/2009 | Howard et al. | |
| 2012/0277794 | A1* | 11/2012 | Kountotsis | A61J 17/10 600/301 |
| 2014/0128691 | A1 | 5/2014 | Olivier | |
| 2016/0166175 | A1 | 6/2016 | Mor et al. | |
| 2017/0055875 | A1 | 3/2017 | Candell et al. | |
| 2019/0120821 | A1 | 4/2019 | Atsalakis | |
| 2020/0022617 | A1* | 1/2020 | Thompson | A61B 5/097 |
| 2021/0085247 | A1* | 3/2021 | Meirav | A61B 5/0833 |
| 2021/0169370 | A1 | 6/2021 | Vicario et al. | |
| 2021/0177301 | A1 | 6/2021 | Buizza et al. | |
| 2022/0193536 | A1* | 6/2022 | Aurongzeb | A63F 13/533 |

FOREIGN PATENT DOCUMENTS

| | | | | |
|---|---|---|---|---|
| WO | WO-2017019783 A1 * | 2/2017 | | A61B 5/0816 |
| WO | WO-2018183215 A1 * | 10/2018 | | A61B 5/0075 |

OTHER PUBLICATIONS

Yang et al., Metal-Oxide gas sensors for exhaled-breath analysis: a review, Measurement Science and Technology, 32, Jul. 2021 (Year: 2021).*

Vajhadin et al., Metal oxide-based gas sensors for the detection of exhaled breath markers, Med Devices Sens. Mar. 29, 2021 (Year: 2021).*

Yueqiang Lin et al, “Compositing strategies to enhance the performance of chemiresistive CO2 gas sensors”, Elsevier, Materials Science in Semiconductor Processing, School of Materials Science and Engineering, China University of Petroleum, Qingdao, 266580, Shandong, PR China.

Noboru Yamazoe et al, “Receptor Function and Response of Semiconductor Gas Sensor”, Hindawi Publishing Corporation, Journal of Sensors, vol. 2009, Article ID 875704, 21 pages.

Ramon Huerta et al, “Online decorrelation of humidity and temperature in chemical sensors for continuous monitoring”, Aug. 8, 2016.

Lupinsky L. et al, “Resting Energy Expenditure (REE) with Mask”, Validation Papers.

Mixing Chamber versus Breath by Breath, Help Center Resources.

Kent A. Lorenz et al, “Validity of the Lumen® hand-held metabolic device to measure fuel utilization in healthy young adults”.

S Jimena Mora et al, “Validation of a wearable metabolic tracker (Breezing ProTM) for Resting Energy Expenditure (REE) measurement via Douglas bag method”, Global Journal of Obesity, Diabetes and Metabolic Syndrome.

Alexander H.K. Montoye et al, “Validity and Reliability of the VO2 Master Pro for Oxygen Consumption and Ventilation Assessment”, International Journal of Exercise Science 13(4): 1382-1401, 2020.

Weir, J. B. D., “New Methods For Calculating Metabolic Rate With Special Reference To Protein Metabolism.” Journal Of Physiology (1949)—London 109(1-2): 1-9.

S.I. Lukash, “Development of the Technique of Measurement of CO2 in Exhaled Air”.

Russian Office Action dated Jul. 22, 2022, issued in Russian Application No. 2021130936/28(065663).

Russian Search Report dated Jul. 22, 2022, issued in Russian Application No. 2021130936/28(065663).

International Search Report dated Feb. 2, 2023, issued in International Application No. PCT/KR2022/016035.

* cited by examiner

DEVICE FOR METABOLISM MONITORING BY MEANS OF MOS SENSOR AND A CORRESPONDING METHOD

CROSS-REFERENCE TO RELATED APPLICATION(S)

This application is a continuation application, claiming priority under § 365(c), of an International application No. PCT/KR2022/016035, filed on Oct. 20, 2022, which is based on and claims the benefit of a Russian patent application number 2021130936, filed on Oct. 22, 2021, in the Russian Intellectual Property Office, the disclosure of which is incorporated by reference herein in its entirety.

TECHNICAL FIELD

The disclosure relates to an ultra-compact, low-cost device for measuring, tracking and analysis of changes in exhaled air associated with metabolism, physical activity, and/or food consumption by individuals, and a corresponding method. The disclosure is intended for personal health care, fitness tracking, and dietary management of a user.

BACKGROUND

Attempts are currently being made to measure and analyze exhaled air and changes in exhaled air composition that may be related to metabolism, physical activity or diet of a user.

One of the known methods for estimating metabolic parameters is indirect (inferential) calorimetry, which measures the ratio between the concentration of oxygen consumed by a person and the concentration of carbon dioxide produced during the metabolic process. However, for indirect calorimetry, as a rule, bulky and expensive devices are used.

For example, known is a device described in U.S. Patent Pub. No. 2009/227887 (2009). This device is a portable metabolic analyzer transducer comprising a housing containing a plurality of analog sensors, an analog-to-digital (A/D) converter, a microcontroller and a power source operatively coupled thereto, where the microcontroller is programmed to compute minute ventilation, oxygen (O2) uptake, and carbon dioxide (CO2) production of a subject. This device is large enough, consumes a lot of energy and therefore is not suitable for use in portable devices. The device uses an Non-Dispersive Infrared Spectroscopy (NDIR) sensor as a CO2 sensor. The NDIR sensor is an optical sensor, which is one or more opto couplers, wherein the elements of the NDIR sensor are spaced from each other, which is a disadvantage due to the sensitivity of this sensor to their location, since the NDIR sensor is essentially a multi-pass cell, and any deformations that are inevitable during the operation of this sensor lead to a decrease in performance of the device. In addition, devices based on NDIR sensors are limited in size, since their size cannot be reduced due to the size of the NDIR sensor itself.

Further, known is a device described in U.S. Pat. No. 10,078,074 (2018). This device is a calorimetric gas sensor that is an optical sensor. The device has a source and a receiver, which are located on opposite sides of a tube through which the analyzed air passes. At that, a chemical coating is applied to one of the sides of the tube, which changes its color upon contact with the analyzed gas. The disadvantage of this solution is that the chemical coating is unstable, degrades over time, gets dirty and the quality of this device may deteriorate.

One more solution is described in International Patent Pub. No. WO 200789328 (2007). This solution provides a system and a method for monitoring endogenous compound concentration in blood by detecting markers, such as odors, upon exhalation by a patient, wherein such markers are the endogenous compound itself or result from the endogenous compound. This system has large size and is inconvenient for use in mobile devices for the mass market.

Another device described in U.S. Pat. No. 7,108,659 (2006) uses a fluorescent oxygen sensor. However, fluorescent sensors are unstable, affected by temperature, humidity, etc.

There is a current need to provide low-cost and energy-efficient metabolic monitoring devices for a user, providing assistance in physical activity and diet planning to balance and optimize energy consumption and energy expenditure during the user's vital activity.

Known from related art is determination of the gases concentration using oxide semiconductor sensors, which comes to measuring a change in electrical resistance of the polycrystalline element of the sensor device, which occurred as a result of its interaction with the determined gas.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a device and a method for metabolism monitoring of a user based on low-cost, energy-effective and ultra-compact MOS sensor.

To resolve the problems described above, the disclosure proposes systems and methods for estimating individual parameters of the user's metabolism using a metal oxide semiconductor (MOS) sensor.

Additional aspects will be set forth in part in the description which follows and, in part, will be apparent from the description, or may be learned by practice of the presented embodiments.

In accordance with an aspect of the disclosure, a device for metabolism monitoring is provided. The device comprises a metal oxide semiconductor (MOS) sensor (110), located in air flow exhaled by a user and configured to output a signal corresponding to a ratio of carbon dioxide concentration in exhaled air to oxygen concentration in inhaled air. The device comprises a processor (120) configured to read the MOS sensor (110) output signal. The processor (120) configured to obtain a Respiratory Exchange Rate (RER) value representing a metabolism parameter from the MOS sensor (110) output signal. The processor (120) configured to output a result of the metabolism monitoring to the user in a text or digital form.

In accordance with an aspect of the disclosure, a method for metabolism monitoring is provided. The method comprises locating a metal oxide semiconductor (MOS) sensor into an air flow exhaled by a user to output a signal corresponding to a ratio of carbon dioxide concentration in exhaled air to oxygen concentration in inhaled air. The method comprises reading the MOS sensor (110) output signal by a processor (120). The method comprises obtaining a Respiratory Exchange Rate (RER) value representing a metabolism parameter from the MOS sensor (110) output signal. The method comprises outputting a result of the metabolism monitoring to the user in a text or digital form.

BRIEF DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DESCRIPTION

Figure 1:
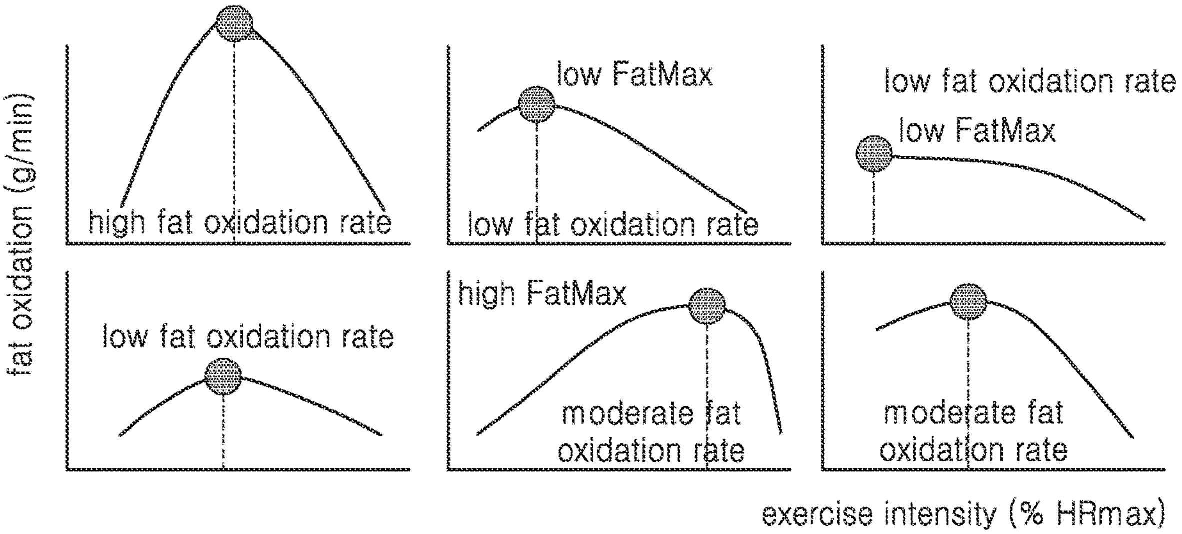
FIG. 1 illustrates the types of curves representing fat burning (oxidation) rate depending on a user's metabolism type according to an embodiment of the disclosure.

The following description with reference to the accompanying drawings is provided to assist in a comprehensive understanding of various embodiments of the disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

It should be understood that the terms "first", "second", etc., can be used herein to describe various elements, these elements should not be limited by these terms. These terms are only used to distinguish one element from another. For example, the first element can be called the second element, and, in the same way, the second element can be called the first element, without limiting the scope of the embodiments. For the purposes of this document, the term "and/or" includes any and all combinations of one or more of corresponding listed elements.

The terminology used herein is intended only to describe the embodiments and is not intended to limit the embodiments. Further, it should be understood that the terms "comprises", "comprising", "includes" and/or "including", when used for the purposes of this document, stipulate the presence of specified features, numbers, steps, actions, elements, components, and/or their groups, but do not exclude presence or addition of one or more other features, numbers, steps, actions, elements, components, and/or their groups.

For the purposes of this document, the term "and/or" includes any and all combinations of one or more of the corresponding listed elements. Expressions such as "at least one of", when they precede the list of elements, change the entire list of the elements and do not change the individual elements of the list.

In an embodiment of the disclosure, a "module" or "block" performs at least one function or action, and may be implemented in hardware, software, or a combination of hardware and software. In addition, a plurality of "modules" or a plurality of "blocks" can be integrated into at least one processor.

The description of the proposed disclosure is presented below with reference to the accompanying drawings.

Planning the user's physical activity and diet comes to providing balancing and optimizing the consumed energy and expenditure of this energy during the user's vital activity. This balance depends on a number of factors, namely nutrition, activity and such parameter as individual metabolism of each user.

One embodiment of the disclosure is based on usage of a metal oxide semiconductor sensor (MOS) that allows performing an indirect calorimetry function. The proposed solution is based on the fact that the MOS sensor signal is proportional to the ratio between oxidizing and deoxidizing gases in the close proximity of this MOS sensor, and when the MOS sensor is placed under certain conditions in exhaled air flow in which carbon dioxide and oxygen are present, the concentration of which prevails over all other gases, the output signal of the MOS sensor located in exhaled air, substantially, is proportional to the ratio of oxygen $O_2$ concentration to carbon dioxide $CO_2$ concentration.

The following approach is considered in the disclosure.

In the typical composition of exhaled air, oxygen and carbon dioxide are of the highest concentrations. The other two gases in exhaled air, namely nitrogen and hydrogen, have, essentially, a carrying function, and their concentration does not change significantly during metabolism process, so their concentration can be taken as a constant value (a constant). This allows to make an assumption, on which the proposed solution is based, namely, in the disclosure considered is that all changes in exhaled air, which are read by the MOS sensor, are primarily associated with changes in the concentration of $CO_2$ and $O_2$.

In addition, due to the small size of the MOS sensors manufactured using MEMS technology, the dimensions of which typically do not exceed 2 mm×2 mm×1 mm, their installation in any portable device, for example, a mask, telephone, watch, is greatly simplified. In this case, the proposed device in a typical implementation contains only a MOS sensor and a processor which outputs at the output an original signal of the MOS sensor, or features derived from the MOS sensor signal, or immediately the desired metabolism parameters.

In a further embodiment, the disclosure is implemented as a system in which the MOS sensor transmits its output signal to a terminal device having a processor, and which is external to the MOS sensor, for example, a mobile phone, which processes the original MOS sensor signal in the corresponding unit. In this case, wireless and/or wired communication is provided between the MOS sensor and the external device.

Examples of Using Indirect Calorimetry $$FOOD + O_2 \rightarrow CO_2 + H_2O + HEAT$$

Obviously, the metabolic process can be analyzed by directly measuring the heat released during food oxidation (direct calorimetry), this method is widely used, however, it is resource-intensive. The second method is indirect calorimetry, which measures the ratio between oxygen, which is spent on oxidizing food, and carbon dioxide, which is released as a result of this oxidation. For this purpose, the proposed solution based on the MOS sensor is used, which allows performing the function of indirect calorimetry.

One of the main indicators of metabolism is the Respiratory Exchange Ratio (RER), which is described by the following relationship:

$$RER = \frac{V_{CO_2(produced)}}{V_{O_2(consumed)}}, \quad \text{Equation 1}$$

wherein the values $V_{CO_2(produced)}$ and $V_{O_2(consumed)}$—are the volumes of, respectively, carbon dioxide produced in the process of metabolism and consumed oxygen. These volumes are, in turn, relating to the concentrations of the corresponding gases and the total volumes of exhaled and inhaled air as follows:

$$V_{CO2produced} = C_{co2_e} V_e - C_{co2_i} V_i \quad \text{Equation 2}$$
$$V_{O2consumed} = C_{o2_i} V_i - C_{o2_e} V_e,$$

wherein $V_e$ and $V_i$—are the volumes of exhaled and inhaled air correspondently, $C_{co2_s}$ and $C_{co2_i}$—concentrations of carbon dioxide in exhaled and inhaled air correspondently, $C_{o2_e}$ and $C_{o2_l}$—concentrations of oxygen in exhaled and inhaled air correspondently. At the same time, the Haldane transform allows to relate the total volumes $V_e$ and $V_i$ of exhaled and inhaled air via corresponding concentrations $C_{co2_e}$, $C_{co2_i}$, $C_{o2_e}$ and $C_{o2_i}$ of carbon dioxide and oxygen as follows:

$$\frac{V_e}{V_i} = \frac{1 - C_{o2_i} - C_{co2_i}}{1 - C_{co2_e} - C_{o2_e}}, \quad \text{Equation 3}$$

Assuming that the total concentration of carbon dioxide and oxygen is constant $C_{o2_l}+C_{co2_i} \cong C_{co2_e}+C_{o2_e}$, the Equations 2 and 3 allow to express the respiratory exchange rate (RER) in terms of concentrations:

$$RER \cong \frac{C_{co2_e} - C_{co2_i}}{C_{o2_i} - C_{o2_e}} \quad \text{Equation 4}$$

Since the concentration of carbon dioxide in exhaled air is much higher than the concentration of carbon dioxide in the inhaled air, $C_{co2_i} \ll C_{co2_e}$, and the concentration of oxygen in the inhaled air changes insignificantly, equation 4 can be reduced:

$$RER \cong \frac{C_{co2_e}}{A - C_{o2_e}} = \frac{C_{o2_e}}{\Delta C_{O2}}, \quad \text{Equation 5}$$

wherein A—a constant proportional to the oxygen concentration in ambient air. Thus, Equation 5 allows estimating the respiratory exchange rate (RER) as a ratio of carbon dioxide to oxygen concentrations in exhaled air without need to directly measure the volumes of exhaled carbon dioxide and inhaled oxygen.

Depending on whether a person burns fats or carbohydrates in the vital activity process, energy is released in different ways, resulting in different reaction products (Jeukendrup A. E., Wallis G. A. Int J Sports Med 2005, 26, S28-S37):

Carb Burn $6\ O_2+C_6H_{12}O_6=6CO_2+6H_2O+$
38 ATP RER=1

Fat Burn $23\ O_2+C_{16}H_{32}O_2=16\ CO_2+16$
$H_2O$+129 ATP RER=0.7

Thus, with the predominant burning of carbohydrates, the ratio of the volume of carbon dioxide produced in the process of vital activity to the volume of consumed oxygen is close to 1, and with the predominant burning of fats, this ratio is close to 0.7. The values of 1 and 0.7 are theoretical limits that are derived from the reaction equations themselves: $6CO_2/6O_2=1$; $16CO_2/23O_2=0.7$.

The actually measured values tend to these limits, but may not be equal to them. Values below 0.7 or more than 1 may also occur, which may indicate any non-standard conditions, or pathologies that are no longer described by the above equations. Situations in which RER can go beyond the specified limits are considered in more detail, for example, in the document Schutz Y., Ravussin E. The American Journal of Clinical Nutrition 1980, 33(6), 1317-1319; Jeukendrup A. E., Wallis G. A. Int J Sports Med 2005, 26, S28-S37; or Triathlon Science, Joe Friel.

Accordingly, when measuring the RER parameter, it is possible to conclude what, namely, is the main source of energy for the user—carbohydrates or fats. The obtained RER values are used to develop recommendations for planning and dosing physical activity and nutrition for the user. The issuance of recommendations to the user can be made, for example, in digital or text form.

Another important parameter characterizing the user's metabolism is the fat burning rate (Fat oxidation rate or simply Fat oxidation). The goal of many fitness activities is to burn fat. Accordingly, it is necessary to select physical activity in such a way that the fat burning process is effective in order to maximize the stimulation of fat burning during physical exercises. Parameter Fat oxidation shows the rate of fat burning (oxidation). This parameter can be approximately derived depending on the intensity of the exercise load as follows:

$$\text{Fat oxidation}\left[\frac{g}{\min}\right] = 1.7\left[\frac{g}{L}\right]\times V_{O2}\left[\frac{L}{\min}\right] - 1.7\left[\frac{g}{L}\right]\times V_{CO2}\left[\frac{L}{\min}\right], \quad \text{Equation 6}$$

wherein $V_{CO2}$ and $V_{O2}$—the volume of output (produced) carbon dioxide and the volume of consumed oxygen, respectively (Jeukendrup A. E., Wallis G. A. Int J Sports Med 2005, 26, S28-S37).

The Equation 6 is just one example of calculating the Fat oxidation parameter.

FIG. 1 shows six types of curves reflecting fat burning (oxidation) depending on the type of metabolism according to an embodiment of the disclosure.

Referring to FIG. 1, the abscissa in these graphs shows intensity of the load, which is estimated by heart rate, and the ordinate is the fat burning rate. During physical exercise, it is preferable to achieve a state of energy expenditure, which is characterized by the most intense fat burning and which corresponds to the point with the maximum value shown on each of the graphs. This state will be different for different people and for different levels of stress. At the same time, if the load is below a certain level, a person does not burn fat enough to maintain his physical shape, and, similarly, if the load is too great, then fat burning is not increased, but is decreased. The fact that by unreasonably increasing the load, fat burning decreases while carb burning increases is common knowledge in fitness. With a high intensity of physical exercises, the rate of fatty acid oxidation in blood plasma decreases, since the blood flow becomes insufficient for transferring the fatty acids from fatty tissue into the systemic circulation. Carbohydrates have twice the rate of energy transfer compared to fatty acids, therefore, under intense loads, their oxidation replaces the process of fat oxidation to a greater extent. (Lorber B., Fischer F., Bailly M., Roy H., Kern D. Biochemistry and molecular biology education, 2012, 40(6), 372-382; Hodgetts V., Coppack S. W., Frayn K. N., Hockaday T. D., J appl Physiol, 1991, 71(2), 445-51). Therefore, the nature of the dependence of the fat burning rate on physical activity shall be considered for dosing the load in fitness.

To measure the above parameters, an appropriate clinical device is required. At present, in addition to large installations requiring the participation of medical personnel, there are attempts to propose a device suitable for the consumer market, but such devices usually use some type of gas sensors for measuring concentrations (or volume fractions) of oxygen and carbon dioxide in exhaled air and subsequent calculating the respiratory exchange rate RER based on Equation 5. For example, sensors based on non-dispersive infrared spectroscopy (NDIR) or sensors based on photoacoustic spectroscopy (PA) can be used to measure carbon dioxide concentration. Both types of sensors use radiation sources of sufficiently high intensity, which can lead to high energy consumption and heating the device. An electrochemical sensor that can be used to measure oxygen concentration degrades over time (the typical life of an electrochemical sensor does not exceed 1-1.5 years) and has a high cost. All of the listed types of sensors are limited in size; they cannot be made smaller due to their design features. In addition, the use of selective sensors designed for measuring a specific gas concentration implies that two separate gas sensors are required to measure RER: one for measuring carbon dioxide and one for measuring oxygen.

To solve said problem, the disclosure proposes the use of a MOS sensor according to the various embodiments described herein.

Figure 2:
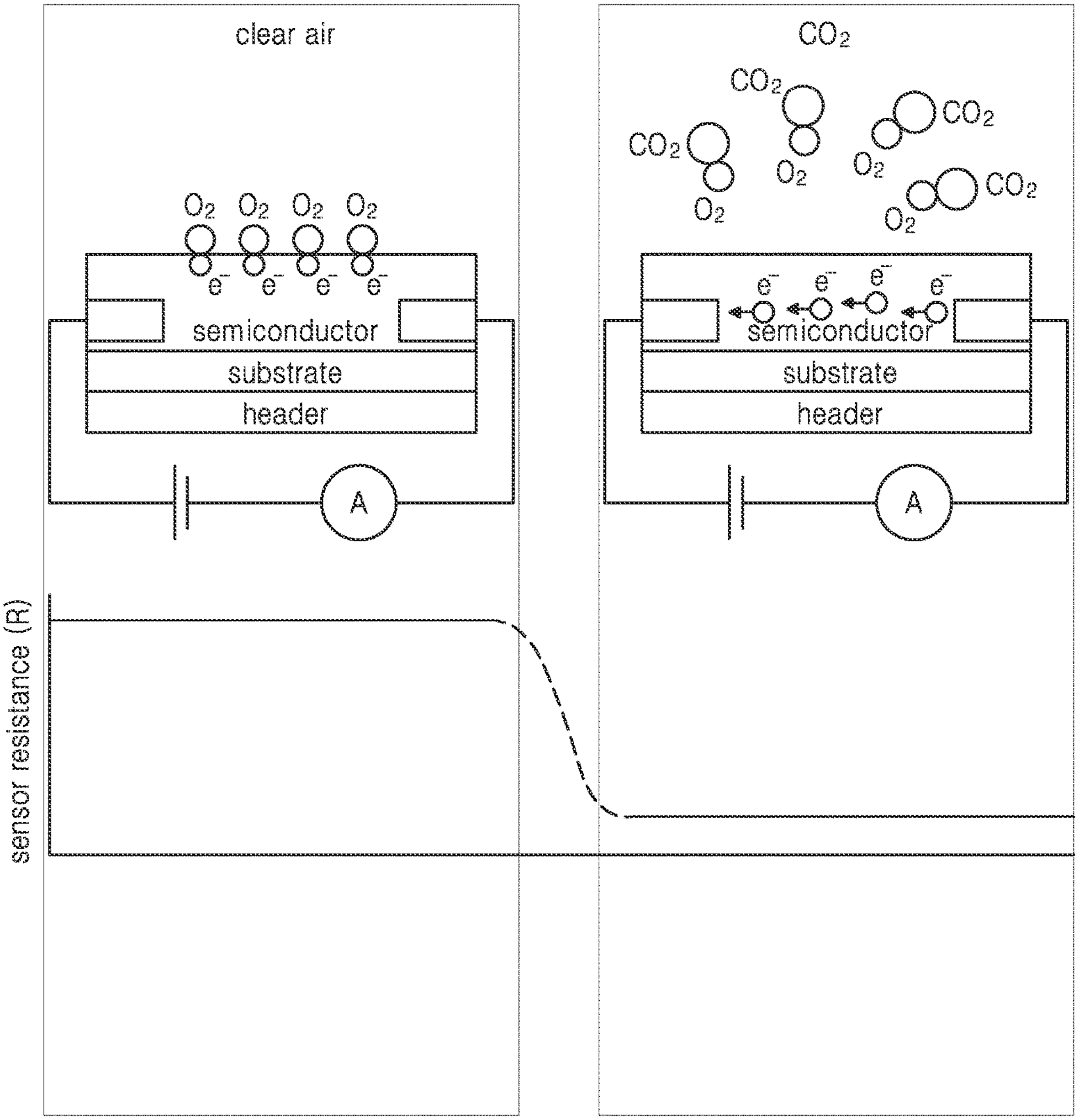
FIG. 2 illustrates an operation principle of a MOS sensor according to an embodiment of the disclosure.

The proposed MOS sensor comprises a semiconductor layer with integrated electrodes, isolated from a heater by a substrate, and the heater itself (see FIG. 2). In conditionally clean air without any impurities or gases, oxygen molecules bind to free carriers (electrons) on the surface and inside the semiconductor layer, while the resistance of the semiconductor layer increases, and the current through the semiconductor layer decreases. When molecules of another gas appear in the air, which is able to bind with oxygen, that is, molecules of a deoxidizing gas, which oxidizes itself, its molecules bind with oxygen, free carriers (electrons) are released, charge carriers appear in the semiconductor layer, its resistance decreases, and the current strength through the semiconductor increases. Thus, the amount of charges, resistance and the amount of current that flows through the semiconductor layer are directly related to the ratio between the concentrations of deoxidizing and oxidizing gases.

Typical dimensions of the MOS sensor manufactured using MEMS technology are approximately 2 mm×2 mm×1 mm, which simplifies its installation in any portable device, for example, a mask, any mobile device, for example, a phone, a watch. That is, the MOS sensor can be built into almost any device, even into small devices.

The Principle of Operation of the Proposed Device

The principle of operation of the MOS sensor can be described by two Equations 7 and 8 below, see also FIG. 2.

$$\frac{\beta}{2}O_{2(g)} + \alpha e^- \leftrightarrow O^{\alpha}_{\beta(ad)}, \quad \text{Equation 7}$$

$$CO_{2(g)} + \frac{1}{\beta}O^{\alpha-}_{\beta(ad)} \leftrightarrow CO_{3(ad)} + \frac{\alpha}{\beta}e^-, \quad \text{Equation 8}$$

wherein α, β—stoichiometric coefficients of the chemical reaction equation on the active surface of the MOS sensor. The index (ad) marks the element adsorbed on the surface. $E^-$—is a free electron in the semiconductor material of the sensor.

In clean air, electrons in the semiconductor layer are bound to oxygen (Equation 7), therefore, there are no free charge carriers, therefore, there is no current in the semiconductor layer, and the resistance of the semiconductor layer is high. In the presence of deoxidizing gases (Equation 8), oxygen is bound to its molecules, and electrons can move freely, therefore, the resistance of the semiconductor layer drops, and current begins to flow through it. In general, the resistance of the MOS sensor is proportional to balance between deoxidizing gases and oxygen. At the same time, the concentration of $CO_2$ in exhaled air prevails over that of all other deoxidizing gases.

In the proposed solution, the semiconductor layer resistance is measured, while it is possible to express the MOS sensor signal, i.e. the resistance value, analytically by two Equations 9 and 10:

$$\frac{R}{R_{baseline}} = \frac{1 + \frac{\sum k_i \cdot C_i^o}{k_{O_2} \cdot C_{O_2}^{0.5}}}{\left(1 + \sum k_i \cdot C_i^R\right)^{0.5}} \qquad \text{Equation 9}$$

$$\log\left(\frac{R}{R_{baseline}}\right) = b + a \cdot RH + c \cdot T \qquad \text{Equation 10}$$

wherein $R_{baseline}$—the initial resistance of the sensor semiconductor layer at zero concentration of $CO_2$. $K_i$ is coefficient of adsorption of the i-th component of the gas mixture, the change in the concentration of which has a significant effect on the sensor resistance. RH, T—respectively, relative humidity and temperature of the analyzed gas mixture. A, b, c—approximation coefficients of the real dependence of the sensor semiconductor layer resistance on the humidity and temperature of the gas mixture (N. Yamazoe et al. Sensors and Actuators B: Chemical, 163(1), 2012; R. Huerta et al. Chemometrics and Intelligent Laboratory Systems, 157(15), 2016).

FIG. 2 illustrates a dependency graph of the semiconductor layer resistance on the balance between $CO_2$ and $O_2$ according to an embodiment of the disclosure.

Referring to FIG. 2, the left side of the graph shows that when electrons are captured by $O_2$ molecules, the resistance R of the sensor is high, and when $CO_2$ molecules react with $O_2$ molecules (on the right side of the graph of FIG. 2), the electrons are released and the resistance R of the sensor drops.

This process depends on the concentration not only of $CO_2$, but any gas capable of binding with oxygen and deoxygenating the semiconductor layer will lead to a change in the resistance of the semiconductor. The above principle of operation is common to all semiconductor sensors.

In accordance with the proposed solution, the MOS sensor is installed in any location in the close proximity of exhaled air flow (medium). The proposed solution is based on several key features.

One feature of the proposed solution is to consider the fact that the calculated RER value according to Equation 5 is proportional to the ratio of $CO_2$ to $O_2$ concentrations. At the same time, the MOS sensor signal is also proportional to the ratio of $CO_2$ to $O_2$ concentrations. Therefore, the MOS sensor signal allows the RER value to be obtained directly without the need to measure the volumes of $CO_2$ in exhaled air and $O_2$ in inhaled air separately, as required by the determination of the respiratory exchange rate according to Equation 1. That is, the output signal of the MOS sensor immediately allows to get the RER value.

Therefore, the RER value can be determined using one signal from one sensor, and there is no need to use two sensors and measure the concentration of two gases separately.

Equations 9 and 10, analytically describing the resistance of the MOS sensor, can be combined into one Equation 11:

$$\frac{R}{R_{baseline}} = \frac{1 + A \cdot \Delta C_{O_2}}{\left(1 + B \cdot C_{CO_2}\right)^{0.5}} \cdot e^{a \cdot RH + c \cdot T} \qquad \text{Equation 11}$$

wherein $R_{baseline}$—initial resistance of the semiconductor layer of the sensor at zero concentration of $CO_2$; RH, T—respectively, the relative humidity and temperature of the analyzed gas mixture; a, c—the approximation coefficients of real dependence of the sensor semiconductor layer resistance on the humidity and temperature of the gas mixture; A and B are the approximation coefficients proportional to the adsorption coefficients k in the Equation 3. Due to proceeding from summation over several gases to one oxidizing gas ($O_2$) and one deoxidizing gas ($CO_2$), respectively, the concentrations of these gases $C_{CO_2}$ and $\Delta C_{O_2}$ only participate in Equation 5, expressed in any accepted measuring units of concentration, for example, parts per million, parts per billion, parts per trillion etc. (ppm, ppb, ppt).

Since the sensor resistance is proportional to the ratio of the deoxidizing to oxidizing gases, and the concentration of $CO_2$ and $O_2$ is the highest of all the deoxidizing and oxidizing gases present in exhaled air flow, only $CO_2$ and $O_2$ are taken into account in this equation of all gases in the performed calculations, since the measured resistance R of the sensor proportional to the $CO_2/O_2$ ratio and the RER parameter is proportional to the $CO_2/O_2$ ratio as well. Therefore, the resistance R of the MOS sensor is proportional to the RER parameter. In general, a calibration curve, an equation describing that curve, or a machine learning model with appropriate coefficients which map the features derived from the MOS sensor signal to specific RER values can be used to determine the RER from the measured MOS sensor signal. In the simplest case, the measured resistance R of the MOS sensor serves as the feature.

Figure 4:
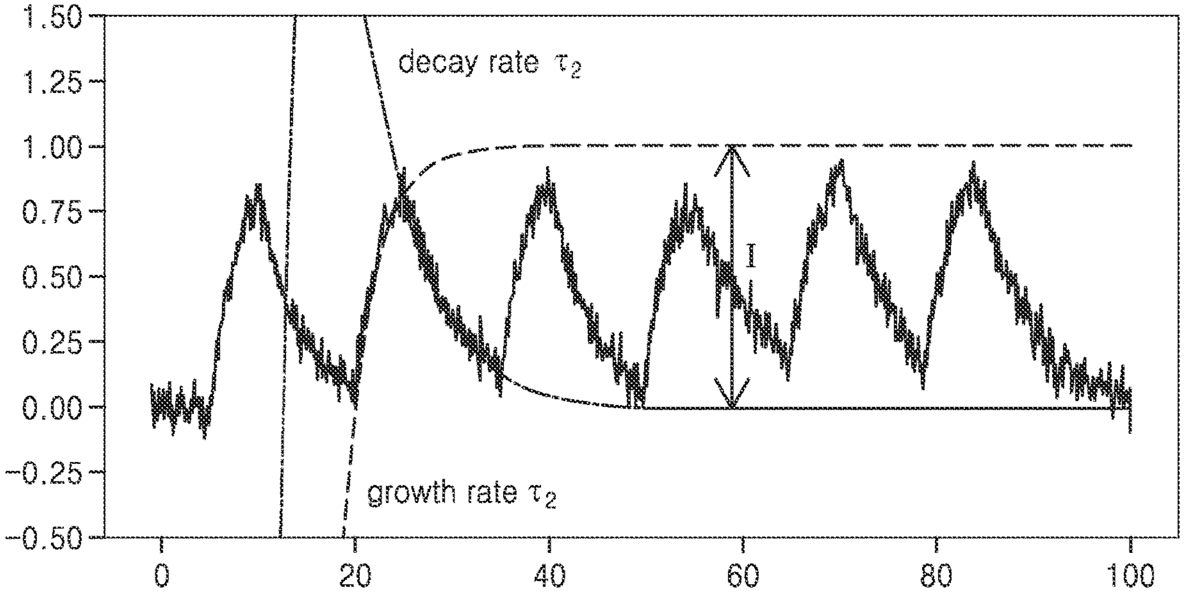
FIG. 4 illustrates a distorted real MOS sensor signal, consisting of several overlapping pulses, each of which corresponds to a separate exhalation during free continuous breathing according to an embodiment of the disclosure.

FIG. 4 illustrates a distorted real MOS sensor signal, consisting of several overlapping pulses, each of which corresponds to a separate exhalation during free continuous breathing according to an embodiment of the disclosure.

Referring to FIG. 4, when the MOS sensor signal is a pulse sequence as shown in FIG. 4, the features can include both the resistance R of the MOS sensor measured at specific points in the pulse (for example, the maximum or minimum of the pulse), and the derived values, such as the rate of growth or decay of the pulse edges. The equation coefficients or machine learning models have the dimensions necessary to translate the corresponding feature into a dimensionless RER value. The operation of translating the features derived from the MOS sensor signal into the RER value can be performed both by the processor included in the proposed solution and by an external device, provided that the device has access to the MOS sensor output data (resistance).

According to the solutions in the related art, two different RER values were obtained using two different sensors, where one sensor was used to measure the $CO_2$ concentration and the second sensor was used to measure the $O_2$ concentration, and then the ratio of said concentrations was found. In the disclosure, it is possible to immediately obtain the $CO_2/O_2$ ratio using only one MOS sensor for at least two cases with different $CO_2$ and $O_2$ ratios when the concentration of these gases in exhaled air changes. Thus, when the concentration of oxygen or carbon dioxide changes during exhalation, a separate sensor is not required to measure the concentration of each of them separately.

Upon receipt of the RER, it is possible to monitor the change of the RER over time. The RER parameter depends on many conditions, for example, RER changes during the day with food intake. When eating, the user's body begins to burn carbohydrates, stopping burning fat, that leads to a change in the RER parameter. How well the body adapts to changes in food ration and/or physical activity is monitored by a "metabolic flexibility" parameter. The Metabolic Flexibility parameter estimates the organism's ability to adapt the oxidation of fats or carbohydrates to those in the organism. In addition, the time it takes to digest food is dependent on the metabolic flexibility. Three typical values of the metabolic flexibility include high flexibility, normal flexibility, and the user's metabolic inflexibility in response to changes in food ration. The better metabolic flexibility, the more efficiently and faster the organism switches between burning fat and burning carbohydrates. Thus, by measuring the RER for some time after food intake, it can be determined that the organism has gone from burning fat to burning carbohydrates. The degree of metabolic flexibility can be determined by how much (amplitude) and how fast (speed) the RER parameter has changed after some effect provided on the digestive system. One of the main problems in measuring metabolic flexibility is, namely, standardization of this effect, be it intravenous administration of nutrients or standardized nutrition with a particular ratio of proteins, fats and carbohydrates. In absence of the established standards and protocols, examples of possible approaches can be found in the literature, for example (D. H. McDougal et al, Obesity, 2020, 28(11); J. E. Galgani et al, Am J Physiol Endocrinol Metab, 2008, 295).

Further, the disclosure can be used, for example, to determine the user's anaerobic threshold using the RER parameter. The anaerobic threshold is the metabolic rate at which lactate production in active muscles exceeds the rate of systemic lactate clearance. Systemic clearance is removal of lactate from blood by processing it in liver and kidney. Determination of the anaerobic threshold can be used to determine whether a person is burning fat or carbohydrates. For example, RER is measured while a person is exercising under controlled exercise. If the RER begins to exceed 1, the anaerobic threshold has been reached. Accordingly, the intensity and duration of the load at which this threshold is reached will be different for people with different constitution. For people with different constitutions, the anaerobic threshold is different and exceeding it for a user with an obese constitution is desirable while training to weight loss, while exceeding the anaerobic threshold for a thin user in this situation is undesirable, since the user begins to burn carbohydrates but not fats. Thus, determination of the anaerobic threshold is necessary for fitness and sports professionals. It can be stated that the anaerobic threshold is an objective measurement that does not depend on the person's constitution, however, how to interpret this measurement depends on the person's constitution.

Figure 3:
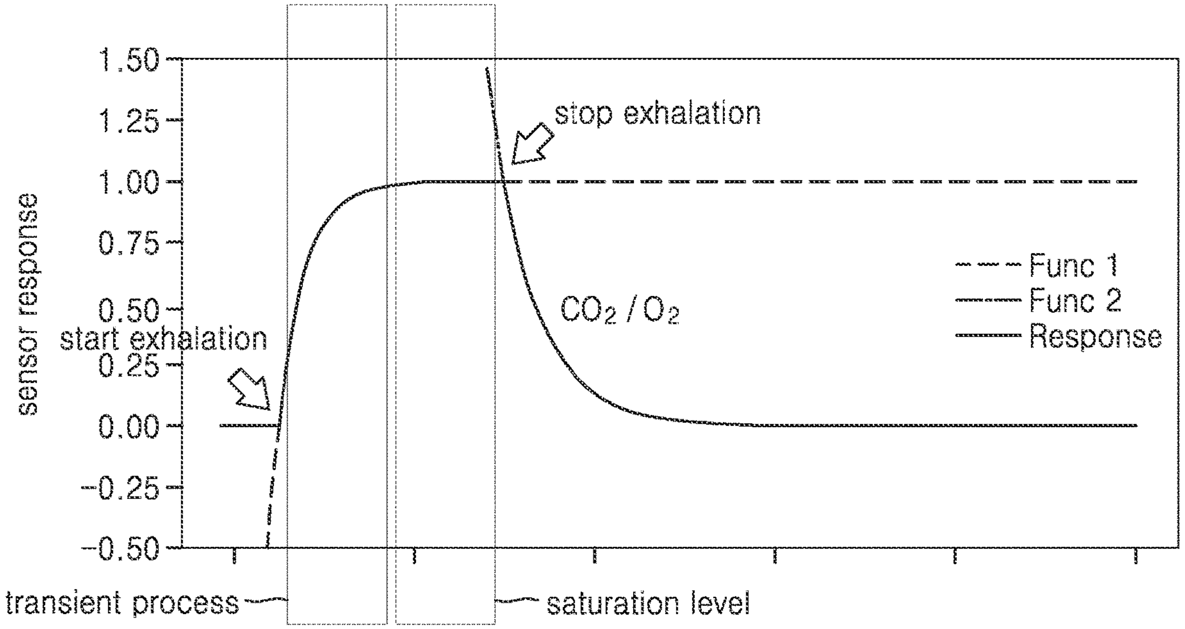
FIG. 3 illustrates an ideal response of a MOS sensor to changes in $CO_2$ and $O_2$ concentrations in one exhalation according to an embodiment of the disclosure.

FIG. 3 illustrates an ideal response of a MOS sensor to changes in $CO_2$ and $O_2$ concentrations in one exhalation according to an embodiment of the disclosure.

Referring to FIG. 3, in an ideal case, the $CO_2$ to $O_2$ concentration ratio curve used in the disclosure is the pulse shown in FIG. 3, where the sensor signal is presented in relative normalized units, but may have, depending on the specific way of including the MOS sensor in the electrical circuit, the dimension of resistance, voltage, or current flowing through the semiconductor layer. The pulse has a rising edge, the so-called dead space, which increases exponentially while the user exhales air from the upper respiratory tract (transient process), and reaches a certain saturation state, in which the air is exhaled mainly from the lower respiratory tract, the so-called end tidal. This section of the curve corresponds to a certain steady state, in which the sensor resistance (maximum value or pulse amplitude) gives the desired ratio of carbon dioxide to oxygen concentrations in exhaled air proportional to RER with a fairly good approximation. When exhalation stops, the gas concentration decreases, and then the MOS sensor resets its state, which is described by the following transient process with an exponentially decaying falling edge of the concentration ratio curve. The shape of this pulse can be described analytically using various equations, for example, using Equation 12

$$func = \begin{cases} 0,\ t < t_0^1 \\ I\left(1 - e^{-\frac{t-t_0^1}{\tau_1}}\right),\ t_0^1 < t < t_0^2 \\ I\left(e^{-\frac{t-t_0^2}{\tau_2}} - e^{-\frac{t-t_0^1}{\tau_1}}\right),\ t > t_0^2 \end{cases} \quad \text{Equation 12}$$

Equation 12 presents the parameters that determine the shape of the pulse: amplitude l, rising edge delay time $$t_0^1,$$

falling edge delay time $$t_0^2,$$

growth rate $\tau_1$, decay rate $\tau_2$.

In other words, the sensor signal or its resistance is always proportional to the ratio of carbon dioxide to oxygen concentration in the environment of this sensor, but the RER parameter is measured correctly only when the saturation level curve shown in FIG. 3 as "end tidal" is achieved. However, the ideal case does not work in practice due to the fact that the MOS sensor has some inertia, that is, its response is delayed, and the ratio curve may not have time to reach the saturation level.

Since in real life breathing is unstable, shallow, then each inhalation-exhalation of the user is described by a non-ideal curve in the form of a single pulse, and the breathing process is actually characterized by a sequence of distorted signals, consisting of overlapping pulses, each of which corresponds to a separate exhalation during free, continuous breathing. Such a sequence is shown in FIG. 4.

Referring to FIG. 3, in order to obtain the correct RER value from the distorted sensor signal, it is necessary to restore the shape of an individual pulse and to determine what maximum amplitude (resistance value) relative to the steady state after exhalation or before exhalation the sensor signal could reach at the saturation section. To this end, the rising edge, shown by the rising dashed line, the falling edge, shown by the falling dashed line, are restored, along these lines the measured amplitude I is restored correctly (more accurately). The approach of restoring the rising and falling edges of the pulse and finding the distance between the base level shown by the falling dashed line, and the saturation level shown by the rising dashed line, gives the amplitude measured correctly. In this case, the amplitude I is proportional to the ratio of $CO_2$ to $O_2$ for a particular pulse from the sequence of pulses. The exact aspect ratio can be determined during the sensor calibration step by comparing the amplitude I with the RER value measured by a reference device. For each of the subsequent pulses, this amplitude correction operation is repeated.

Thus, by calculating the growth rate and the decay rate and substituting the calculated results into Equation 12, the amplitude I of the signal can be determined, with the amplitude I being proportional to the ratio of $CO_2$ to $O_2$ and, therefore, to the respiratory exchange rate (RER).

These operations can be performed both by the processor of the proposed device and by the software of the terminal device, for example, a mobile phone.

Figure 5:
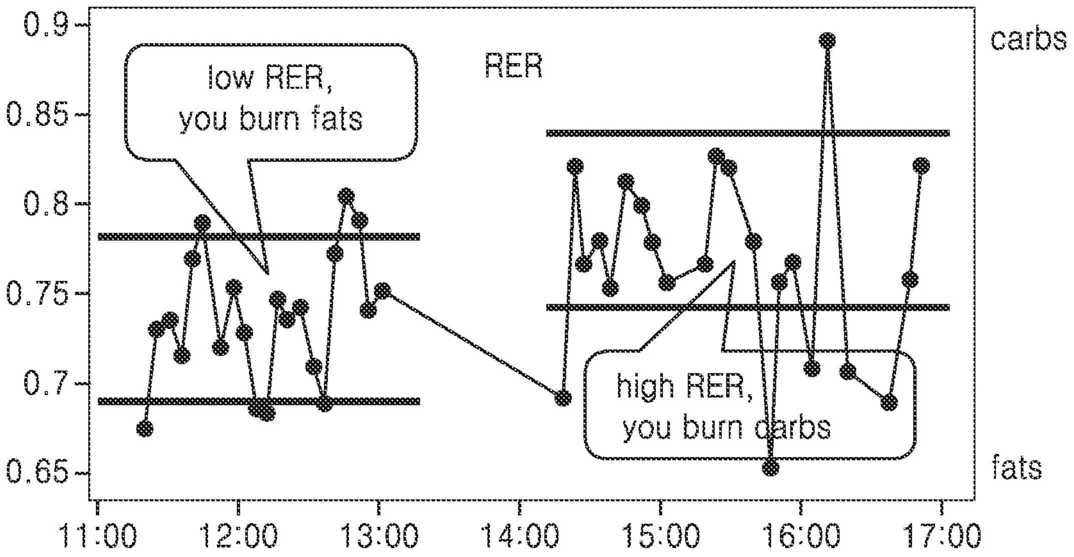
FIG. 5 illustrates a time dependence of the RER parameter calculated for each pulse from the pulses obtained by splitting a MOS sensor signal according to an embodiment of the disclosure.

FIG. 5 illustrates a time dependence of the RER parameter calculated for each pulse from the pulses obtained by splitting a MOS sensor signal according to an embodiment of the disclosure.

Figure 6:
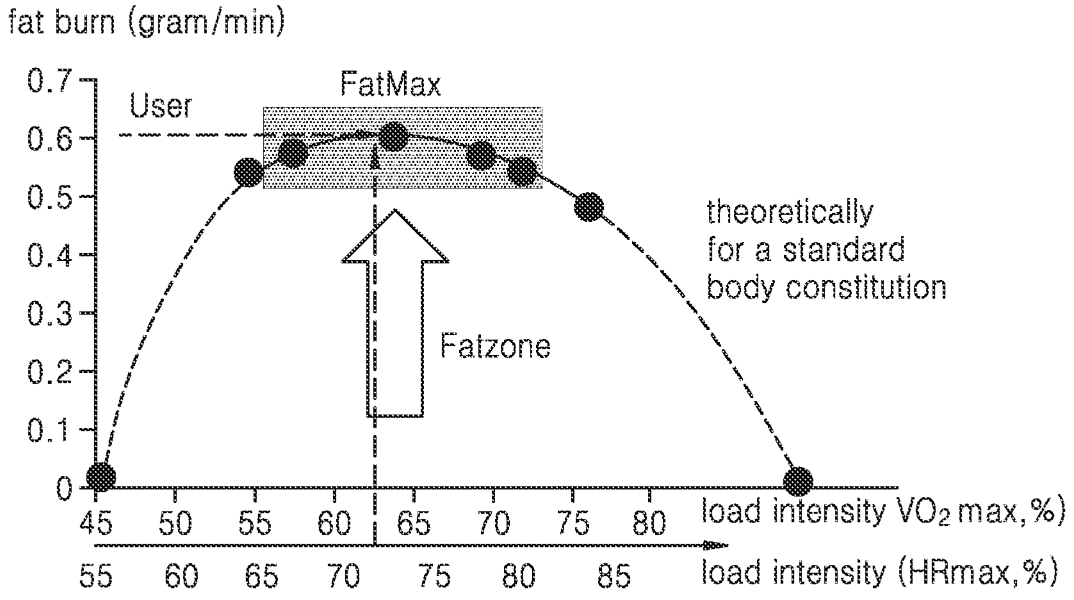
FIG. 6 illustrates a dependence of fat burning rate on exercise intensity according to an embodiment of the disclosure.

FIG. 6 illustrates a dependence of fat burning rate on exercise intensity according to an embodiment of the disclosure.

Referring to FIGS. 5 and 6, at the next step, the resulting pulse sequence shown in FIG. 4 can be handled in two ways. The first approach is to cut the MOS sensor signal into separate pulses, while for each of the pulses the above procedure described by means of Equation 12 is performed, and the amplitude I is calculated. For each of the pulses, the RER value can be calculated and, accordingly, the time dependence of the calculated RER can be constructed, as shown in FIG. 5, where the time is indicated on the abscissa and the RER value—on the ordinate. Each point on the curve represents one pulse that has been processed and for which the RER parameter has been calculated. The MOS sensor signal is proportional to the ratio of oxidizing to deoxidizing gases concentration (in our case, only CO2 to O2), and at the same time, both the growth rate of the signal (edges) and the maximum value that the signal can receive (i.e. amplitude) depend on the concentration. Calibration or machine learning algorithm shows that some combination of edges and amplitude corresponds to some RER.

In another implementation, the original signal received from the MOS sensor is cut into pulses in the processor or on the terminal device, and the average pulse is calculated over a certain period of time, then a procedure for determining the amplitude, edges, etc. is performed for this averaged pulse, and the average RER is calculated over said certain period of time, for example, day, week, etc.

Note that the MOS sensor resistance described by Equation 5 has an exponential part $e^{a*RH+c*T}$, indicated as T/RH (see Equation 13 below), which was considered previously as a constant, and all calculation have been made with accuracy up to this constant.

Equation 13

$$\frac{R}{R_{baseline}} = \underbrace{\frac{1 + A \cdot \Delta C_{O_2}}{(1 + B \cdot C_{CO_2})^{0.5}}}_{RER} \cdot \underbrace{e^{a \cdot RH + c \cdot T}}_{T/RH}$$

Therefore, according to another embodiment of the disclosure, the proposed device based on the MOS sensor allows this factor to be considered, since the proposed device has a heating element that can operate at different temperatures, that affects the value of the coefficients in Equation 11, for example, the basic resistance $R_{baseline}$, calibration coefficients A, B. Accordingly, at different temperatures (Th1 and Th2) of the heating element, the values of resistance R will differ, and different signals will be obtained from the MOS sensor.

$$Th1: R'_{baseline}, A', B' \to R'$$

-continued $$Th2: R''_{baseline}, A'', B'' \to R''$$

As a result of measuring different signals of the MOS sensor at different temperatures of the heating element, a system 14 of two equations is obtained, each for one of at least two values of the temperature Th of the heating element.

Equation 14

$$\begin{cases} R' = f(RER, T/RH, R'_{baseline}, A', B') \\ R'' = f(RER, T/RH, R''_{baseline}, A'', B'') \end{cases}$$

wherein R', R"—the MOS sensor resistance values.

The RER parameter and the exponential factor of Equation 11 are calculated using system 14, which makes it possible to take into account the effect of temperature and relative humidity of the analyzed air flow, using either a processor that is a part of the sensor, or an external device, for example, a mobile phone.

In exhaled air, the relative humidity can reach approximately 100%, which is a problem for most known sensors due to possible moisture condensation and damage to the sensor, or saturation of the sensor and the sensor signal goes out of the dynamic range. To eliminate this problem, additional devices are needed to remove moisture from the air. However, this problem is absent for the present solution, firstly, due to the principle of operation of the MOS sensor, which uses a heating element, therefore, moisture condensation does not occur at a sufficiently high temperature. Secondly, despite the high relative humidity of the expiratory air and, accordingly, the influence of the second factor in Equation 11 on the measured signal, it is possible to directly measure the degree of this influence according to the algorithm described above.

Thus, there is no need to control the humidity during the entire operation of the MOS sensor, while the humidity of exhaled air can reach 100%.

Another embodiment of the disclosure provides a method for estimating metabolism, which has the advantages of the proposed solution described above regarding the lack of the need to monitor the humidity of exhaled air when using the MOS sensor. Additionally, in this embodiment, the T/RH value is not calculated, but is directly measured by any additional sensor that allows you to measure humidity: for example, optical, resistive, electrolytic, thermistor, capacitive, or any other that may be invented in the future. Then the measurements are used to calculate the RER from Equation 5.

Yet another embodiment provides a method for estimating metabolism using multiple MOS sensors rather than a single MOS sensor.

The essence of this embodiment is that when a certain value is measured once or several times by different sensors, different values are obtained, then a certain average value is calculated, and the measurement error can be calculated. Thus, with more measurements, a more accurate calculation of the RER parameter can be obtained.

Different sensors respond differently to the same activation; some sensors are more sensitive and better at detecting low gas concentrations, some sensors have a wider dynamic range and better detect high gas concentrations, while some sensors are less or more inert, due to that the reaction rate of the sensor coincides with dynamics of changes in the concentration of gases in exhaled air flow and, accordingly, the transient processes are measured with less error, then the measurement by several sensors simultaneously is equal to several measurements, and additional data is obtained for multivariate analysis. Thus, by combining several sensors with different characteristics and processing their output signals, a more accurate calculation of the RER parameter is obtained.

In yet another embodiment, a method for estimating metabolism is provided using a MOS sensor and an additional pressure sensor or flow sensor. The use of these sensors allows, firstly, to monitor the volume of inhaled and exhaled air, which results in a more accurate calculation of the RER parameter. Secondly, to continue from the concentrations of carbon dioxide and oxygen to the volumes of these gases, according to Equations 2 and 3, and to calculate new parameters that require an accurate volume value.

In this case, the pressure or flow sensors are used to estimate the volumes of inhaled and exhaled air included in Equation 6. According to the related art, for example, the volume of exhaled air can be estimated as the product of the flow, or air expenditure, and the expiratory time. The air expenditure or flow, in turn, can be either approximately measured using a flow sensor, or estimated in proportion to the pressure drop across the two sections of the air flow, which in turn can be measured using a pressure sensor. In most cases of the measurements, the sensors are in a limited volume, a direct analytical solution to the problem of estimating volumes is not required, sometimes sufficient is to calibrate the sensor or a machine learning algorithm that takes into account the data of pressure and/or flow sensors in the model, etc.

One of the parameters that requires knowledge of the exact volumes of carbon dioxide and oxygen, resting energy expenditure (REE), is the energy expenditure at rest. The parameter REE is calculated by the J. B. D. Weir Equation 15, known, for example, from the source "New Methods For Calculating Metabolic Rate With Special Reference To Protein Metabolism". London Journal of Physiology, J. B. D. Weir (1949). 109 (1-2): 1-9. The REE parameter shows the energy consumed in a resting state, in contrast to the RER parameter, which changes rapidly depending on external conditions, for example, eating, performing an action. The REE parameter does not change quickly, but it is necessary in order to characterize the metabolic parameters more accurately, and is calculated by the Equation:

Equation 15

$$REE\left[\frac{\text{kcal}}{\text{day}}\right] = 1440\times\left[3.9\left[\frac{\text{kcal}}{L}\right]\times V_{O2}\left[\frac{L}{\text{min}}\right]+1.1\left[\frac{\text{kcal}}{L}\right]\times V_{CO2}\left[\frac{L}{\text{min}}\right]\right],$$

wherein 1440 minutes in day and night, $V_{O2}$ and $V_{CO2}$—the volume of inhaled oxygen and the volume of exhaled carbon dioxide, respectively. (Jeukendrup A. E., Wallis G. A. Int J Sports Med 2005, 26, S28-S37). In this case, Equation 15 is just one example of calculating the parameter REE.

Using Equations 1-5 and corresponding assumptions, it can be shown that, when using the MOS sensor to measure RER and additionally measured volumes $V_i$ and $V_e$ of the inhaled and/or exhaled air, the REE parameter can be estimated accurately to the average typical value of oxygen concentration in exhaled air, as follows:

$$REE \approx V(a+b\cdot RER)C,$$

wherein the following continues from the Equation 15:

$$V\approx V_i\approx V_e,\ a=1440\cdot 3.9\left[\frac{\text{kcal}}{L}\right],\ b=1440\cdot 1.1\left[\frac{\text{kcal}}{L}\right],$$

C—a constant proportional to the typical value of the oxygen concentration in exhaled air at rest, adopted for given category of user.

The next parameter that can be calculated using a pressure sensor or a flow sensor for calculating the volumes of the inhaled and exhaled air is the fat burning rate, Fat oxidation, described by Equation 6.

Similar to the parameter REE, it can be shown that in the case of using the MOS sensor, Equation 6 can be represented as:

$$\text{Fat oxidation} \approx V\cdot(a-b\cdot RER)\cdot C.$$

Another additional parameter that can be calculated with a known volume of the inhaled and exhaled air is the carb burning rate, Carb oxidation. This parameter is calculated by the formula:

Equation 16

$$\text{Carb oxidation}\left[\frac{\text{g}}{\text{min}}\right] = 4.6\left[\frac{\text{g}}{L}\right]\times V_{CO2}\left[\frac{L}{\text{min}}\right]-3.2\left[\frac{\text{g}}{L}\right]\times V_{O2}\left[\frac{L}{\text{min}}\right]$$

Similar to the REE parameter, it can be shown that in case of using the MOS sensor, this equation can be represented as:

$$\text{Carb oxidation} = V\cdot(a\cdot RER-b)\cdot C$$

wherein, continuing from Equation 16:

$$V\approx V_i\approx V_e,\ a=4.6\left[\frac{\text{g}}{L}\right],\ b=3.2\left[\frac{\text{g}}{L}\right],$$

C—a constant proportional to the typical value of the oxygen concentration in exhaled air at rest, adopted for given category of user.

A further embodiment provides a method for estimating metabolism using a pre-concentrator for pre-accumulating air exhaled by a user, that is, a device containing a reservoir for collecting a portion of exhaled air. In this case, the flow of exhaled air in natural conditions is not measured directly during breathing, but firstly, a portion of exhaled air is collected into a reservoir, and then the collected air is pumped through a device containing gas sensors. This method allows to stabilize the measurement conditions, eliminate moisture in exhaled air, stabilize the concentration of gases in the air flow pumped through the pre-concentrator reservoir, thereby increasing the measurement accuracy.

An additional embodiment provides a method for estimating metabolism of the above embodiments using machine learning techniques. In one approach of this embodiment, pulse parameters such as amplitude I, growth and decay rates, and edge delays are manually calculated from the MOS sensor signal, and by using these parameters as features or variables for machine learning models, classifying the types of the obtained MOS sensor signals. In another approach, alternatively, to calculate the parameters, an algorithm is used to automatically (blindly) derive the features from the obtained MOS sensor signal, and then the automatically calculated features by some algorithm are fed to the input of another algorithm to classify this signal.

Another embodiment provides a method for estimating metabolism using activity and exercise data previously entered by a user. Since the total energy expenditure is a sum of the REE parameter value, which represents the energy expenditure at rest, which is measured by the sensor, and the user's physical activity, additional information is required to estimate the physical activity, which can be obtained by a smart device that provides information about the user's activity, for example, a smart watch with a built-in heart rate sensor, gyroscope, and/or accelerometer. At the same time, the smart device well determines the moment of start of the user's activity, the duration of this activity, etc. and physical load. Then the obtained information about the user's activity is corrected using such personal parameters as age, constitution of the user, and using these obtained parameters, the total energy expenditure can be calculated. Additionally, using a smart device (a smart watch), the number of meals is counted, the obtained energy is estimated.

Another type of data that is impossible to be measured independently of the user, and it is needed for the user to enter this data himself, is personal information, for example, age, weight, height, etc. This information is necessary for correcting the user's physical activity data.

For example, a parameter such as REE can be calculated theoretically based on data on the user's constitution (weight, height) and his/her age using the Harris-Benedict equation (J A Harris and F G Benedict, Proc. Nat'l. Acad. Sci. USA 1918, 4 (12)). This approach is often used when planning physical activity or drawing up a meal plan: the amount of calories consumed should be in balance with the intensity of physical load and the energy required to maintain organism functions in rest state. However, the theoretically calculated REE may differ from the actually measured REE both upward and downward. If the actual REE measured by the sensor is higher than the theoretical estimation, and the calories for the meal plan were calculated using the theoretical REE, this means that the user is consuming fewer calories than he/she needs. On the other hand, if the actual REE is less than the theoretical estimation, and the meal plan is still based on the theoretical estimation, this means that the user is consuming an excessive amount of calories and this excess will accumulate in his/her body if not spent on additional physical activity. In general, the discrepancy between the theoretically calculated REE and the actual value measured with the sensor, the discrepancy between energy expenditure at rest and the user's biometric data may indicate metabolic disturbance and serve as a reason for a more detailed study by a specialized professional.

Thus, it is possible to continuously and without additional efforts on the user's part, without distracting the user, monitor the energy balance, that is, the amount of received and consumed energy, using additional data from another device, or manually entered by the user.

Thus, the proposed solution operates in various breathing conditions to measure the balance of fats/carbohydrates by the output signal of the MOS sensor and does not require any specific requirements from the user for sampling exhaled air.

Various illustrative logic blocks and schemes described in the embodiments of this application may implement or control the described functions using a general-purpose processor, digital signal processor, application specific integrated circuit (ASIC), field programmable gate array (FPGA), or another programmable logic device, discrete logic gate or transistor, discrete hardware component, or any combination thereof. The general-purpose processor may be a microprocessor. Optionally, the general-purpose processor can alternatively be any conventional processor, controller, microcontroller, or state machine. Alternatively, the processor may be implemented by a combination of computing devices such as a digital signal processor and a microprocessor, a plurality of microprocessors, one or more microprocessors with a digital signal processor core, or any other similar configuration.

Figure 7:
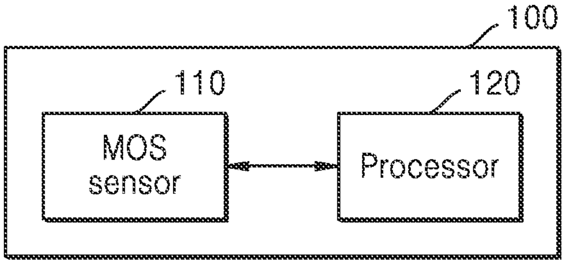
FIG. 7 is a schematic diagram of a device for metabolism monitoring according to an embodiment of the disclosure.

FIG. 7 is a block diagram of a device for metabolism monitoring according to an embodiment of the disclosure.

Referring to FIG. 7, the device for metabolism monitoring 100 may include a MOS sensor 110 and a processor 120.

The MOS sensor 110 may be located in air flow exhaled by a user and configured to output a signal corresponding to a ratio of carbon dioxide concentration in exhaled air to oxygen concentration in inhaled air.

The processor 120 controls all operations of the device for metabolism monitoring 100 and may be used in the same sense as a controller.

The processor 120 may control all the operations of the device for metabolism monitoring 100 and a flow of signals between the internal components of the device for metabolism monitoring 100 and perform a function of processing data.

The processor 120 may include RAM (not shown) that stores signals or data input from outside of the device for metabolism monitoring 100 or is used as a storage area corresponding to various operations performed by the asset management device 100, and ROM (not shown) that stores a control program for controlling the device for metabolism monitoring 100.

Furthermore, the processor 120 may include a plurality of processors.

For example, the processor 120 may be implemented as a main processor (not shown) and a sub processor (not shown) operating in a sleep mode.

In addition, the processor 120 may include at least one of a central processing unit (CPU), a graphic processing unit (GPU), or a video processing unit (VPU).

The processor 120 may read the MOS sensor(110) output signal.

The processor 120 may obtain a Respiratory Exchange Rate (RER) value representing a metabolism parameter from the MOS sensor(110) output signal.

The processor 120 may output a result of the metabolism monitoring to the user in a text or digital form.

Figure 8:
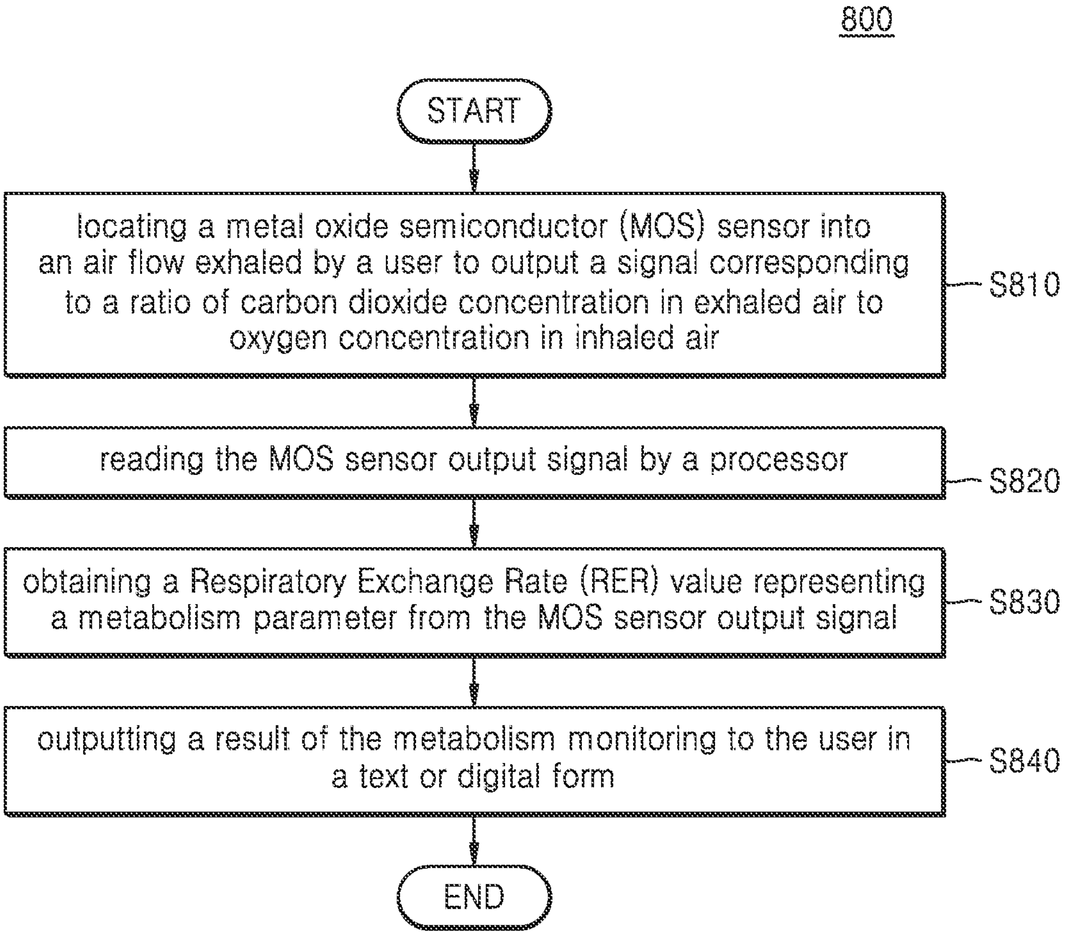
FIG. 8 is a flow diagram of method for metabolism monitoring according to an embodiment of the disclosure.

FIG. 8 is a flow diagram of method for metabolism monitoring according to an embodiment of the disclosure.

Referring to FIG. 8, the device for metabolism monitoring 100 may locate a metal oxide semiconductor (MOS) sensor into an air flow exhaled by a user to output a signal corresponding to a ratio of carbon dioxide concentration in exhaled air to oxygen concentration in inhaled air(S810).

The device for metabolism monitoring 100 may read the MOS sensor(110) output signal by a processor(120)(S820).

The device for metabolism monitoring 100 may obtain a Respiratory Exchange Rate (RER) value representing a metabolism parameter from the MOS sensor(110) output signal(S830).

The device for metabolism monitoring 100 may output a result of the metabolism monitoring to the user in a text or digital form(S840).

A detailed description of each step was described above with reference to FIG. 1-7.

In accordance with an aspect of the disclosure, a device for metabolism monitoring is provided. The device comprises a metal oxide semiconductor (MOS) sensor (110), located in air flow exhaled by a user and configured to output a signal corresponding to a ratio of carbon dioxide concentration in exhaled air to oxygen concentration in inhaled air. The device comprises a processor (120) configured to read the MOS sensor (110) output signal. The processor (120) configured to obtain a Respiratory Exchange Rate (RER) value representing a metabolism parameter from the MOS sensor (110) output signal. The processor (120) configured to output a result of the metabolism monitoring to the user in a text or digital form.

The processor(120) is further configured to process a signal as a pulse of the MOS sensor(110) for each inhalation/exhalation by reconstructing rising and falling edges of the pulse of said signal, and determine an amplitude value between a steady state of the sensor signal after the exhalation or before the inhalation and a saturation level of the signal, the amplitude value corresponds to the ratio of carbon dioxide concentration in exhaled air to oxygen concentration in inhaled air.

The processor(120) is further configured to read at least two output signals of the MOS sensor(110) at different temperature values of a heating element and different values of relative humidity of the exhaled air, and calculate the RER value based on said read at least two output signals of the MOS sensor(110).

The device comprises at least one additional MOS sensor (110), and the processor(120) is further configured to read an output signal of the at least one additional MOS sensor(110) placed into air flow exhaled by the user for obtaining corresponding RER values, and calculate a mean value of RER based on the obtained RER values of each of the MOS sensors(110).

The processor (120) is further configured to calculate an additional metabolism parameter representing a Resting energy expenditure (REE) value, based on measured volumes of inhaled and exhaled air.

The processor (120) is further configured to calculate an additional metabolism parameter representing fat burning rate value, based on measured volumes of inhaled and exhaled air.

The processor (120) is further configured to calculate an additional metabolism parameter representing carb burning rate value, based on measured volumes of inhaled and exhaled air.

The processor(120) is further configured to obtain several RER parameters during some period of time after the user has eaten food, and determine a metabolic flexibility based on the obtained RER parameters, and typical values of the metabolic flexibility include high flexibility, normal flexibility, and metabolic inflexibility of the user, and monitor adaptation of the user to changes in food ration and/or physical activity based on the metabolic flexibility.

The processor(120) is further configured to obtain several RER values in a process of physical exercising of the user with controlled physical activity during some period of time, and determine the user's anaerobic threshold based on the obtained RER values, usage of the anaerobic threshold for determining whether the user burns fats or carbohydrates.

The device further comprises pre-concentrator for pre-accumulating the air exhaled by the user, and the processor (120) is further configured to collect a portion of the air exhaled by the user in a reservoir of the pre-concentrator, and pump the portion of the collected portion of the exhaled air through the device for metabolism monitoring, comprising the MOS sensor(110).

In accordance with an aspect of the disclosure, a method for metabolism monitoring is provided. The method comprises locating a metal oxide semiconductor (MOS) sensor into an air flow exhaled by a user to output a signal corresponding to a ratio of carbon dioxide concentration in exhaled air to oxygen concentration in inhaled air. The method comprises reading the MOS sensor (110) output signal by a processor (120). The method comprises obtaining a Respiratory Exchange Rate (RER) value representing a metabolism parameter from the MOS sensor (110) output signal. The method comprises outputting a result of the metabolism monitoring to the user in a text or digital form.

The method comprises processing a signal as a pulse of the MOS sensor(110) for each inhalation/exhalation by reconstructing rising and falling edges of the pulse of said signal and determining an amplitude value between a steady state of the sensor signal after the exhalation or before the inhalation and a saturation level of the signal, the amplitude value corresponds to the ratio of carbon dioxide concentration in exhaled air to oxygen concentration in inhaled air.

The method comprises reading at least two output signals of the MOS sensor(110) at different temperature values of a heating element and different values of relative humidity of the exhaled air and calculating the RER value based on said read at least two output signals of the MOS sensor(110).

The method comprises reading an output signal of at least one additional MOS sensor (110) placed into the air flow exhaled by the user for obtaining corresponding RER values and calculating a mean value of RER based on the obtained RER values of each of the MOS sensors (110).

The method comprises calculating an additional metabolism parameter representing a resting energy expenditure (REE) value, based on measured volumes of inhaled and exhaled air.

The method comprises calculating an additional metabolism parameter representing fat burning rate value, based on the measured volumes of inhaled and exhaled air.

The method comprises calculating an additional metabolism parameter representing carb burning rate value, based on the measured volumes of inhaled and exhaled air.

The method comprises obtaining several RER parameters during some period of time after the user has eaten food, determining a metabolic flexibility based on the obtained RER parameters, typical values of the metabolic flexibility include high flexibility, normal flexibility and metabolic inflexibility of the user and monitoring adaptation of the user to changes in food ration and/or physical activity based on the metabolic flexibility.

The method comprises obtaining several RER values in a process of physical exercising of the user with controlled physical activity during some period of time, determining the user's anaerobic threshold based on the obtained RER values, using the anaerobic threshold for determining whether the user burns fats or carbs.

The method comprises using a pre-concentrator for pre-accumulating the air exhaled by the user, collecting some portion of the air exhaled by the user in a reservoir of the pre-concentrator, pumping said portion of the collected exhaled air through the device for metabolism monitoring, comprising the MOS sensor.

In accordance with an aspect of the disclosure, a method for metabolism monitoring is provided. The method comprises locating a metal oxide semiconductor (MOS) sensor into air flow exhaled by a user to output a signal corresponding to a ratio of carbon dioxide concentration in exhaled air to oxygen concentration in inhaled air, transmitting the MOS sensor output signal via wireless or wired communication to an electronic processing unit being external to the MOS sensor, obtaining a Respiratory Exchange Rate (RER) value representing a metabolism parameter by the electronic processing unit, outputting a result of the metabolism monitoring to the user in a text or digital form by the electronic processing unit.

In accordance with an aspect of the disclosure, a metabolic monitoring system is provided. The metabolic monitoring system includes a metal oxide semiconductor (MOS) sensor located in air flow exhaled by a user and configured to output a signal corresponding to a ratio of carbon dioxide concentration in exhaled air to oxygen concentration in inhaled air, and a processor configured to read MOS sensor output signal, obtain a Respiratory Exchange Rate (RER) value representing a metabolism parameter from the MOS sensor output signal, and output a result of the metabolism monitoring to the user in a text or digital form. The processor can be enclosed in a single housing together with the MOS sensor, or it can be implemented in a device external to the MOS sensor.

The processor is configured to derive at least one feature from the signal, then, using an algorithm or on the basis of a calibration curve, to compare said feature with a determined RER value, or a ratio of the produced carbon dioxide volume to the consumed oxygen volume.

In accordance with another aspect of the disclosure, a method for metabolism monitoring is provided. The method includes locating a MOS sensor an air flow exhaled by a user to output a signal corresponding to a ratio of carbon dioxide concentration in exhaled air to oxygen concentration in inhaled air, reading the MOS sensor output signal of by a processor, obtaining a Respiratory Exchange Rate (RER) value representing a metabolism parameter from the MOS sensor output signal, and outputting a result of the metabolism monitoring of a user based on the determined RER.

The obtained RER values or temporal dynamics of RER changes during physical activity or after eating a certain type of food, for example, containing predominantly fats or carbohydrates, are then used to calculate additional metabolism parameters by the processor (hardware, software or software-hardware, etc.) included in the proposed device.

In accordance with another aspect of the disclosure, a method is provided. The method includes monitoring metabolism using multiple MOS sensors.

In accordance with another aspect of the disclosure, a method is provided. The method includes monitoring metabolism using an additional pressure sensor and/or flow sensor.

In accordance with another aspect of the disclosure, a method is provided. The method includes monitoring metabolism using additional parameters such as resting energy expenditure, fat oxidation, carb oxidation to calculate a metabolism RER parameter.

In accordance with another aspect of the disclosure, a method is provided. The method includes monitoring metabolism using a pre-concentrator to pre-accumulate exhaled air.

In accordance with another aspect of the disclosure, a method is provided. The method includes monitoring metabolism using machine learning techniques.

In accordance with another aspect of the disclosure, a method is provided. The method includes monitoring metabolism using data previously entered by a user using a smart device.

Other aspects, advantages, and salient features of the disclosure will become apparent to those skilled in the art from the following detailed description, which, taken in conjunction with the annexed drawings, discloses various embodiments of the disclosure.

While this application has been described with reference to specific functions and their embodiments, it will be appreciated that various modifications and combinations can be made therein without departing from the spirit and scope of this application. Accordingly, the description and accompanying drawings are merely descriptions of this application, as defined by the appended claims, and are considered to be any or all modifications, variations, combinations, or equivalents that encompass the scope of this application. It is clear that a person skilled in the art can make various modifications and changes to this application without departing from the scope of this application. This application is intended to cover these modifications and variations of this application provided that they come within the scope of protection defined by the following claims and their equivalent technologies.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A device for metabolism monitoring, the device comprising:

a metal oxide semiconductor (MOS) sensor positioned in an air flow path through the device for air exhaled or inhaled by a user and configured to output a signal corresponding to a ratio of carbon dioxide concentration in exhaled air to oxygen concentration in inhaled air; and a processor configured to:

read the signal output by the MOS sensor, process the signal during successive inhalation and exhalation cycles of the user, identify, from the signal, a transition between inhalation and exhalation cycles, process the signal as a pulse of the MOS sensor for each inhalation or exhalation based on a temporal response characteristic of the MOS sensor by reconstructing rising and falling edges of the pulse of the signal, calculate an amplitude value between a steady state of the signal of the MOS sensor after the exhalation or before the inhalation and a saturation level of the signal, wherein the amplitude value corresponds to the ratio of carbon dioxide concentration in exhaled air to oxygen concentration in inhaled air, and wherein the reconstructing of the rising and falling edges compensates for a response delay and a signal overlap between successive inhalation and exhalation cycles of the MOS sensor, wherein the reconstructing of the rising and falling edges is performed based on the temporal response characteristic of the MOS sensor and separates signals corresponding to successive inhalation and exhalation cycles, wherein the amplitude value is determined based on the signal after compensation of the response delay and signal overlap, calculate a Respiratory Exchange Rate (RER) value representing a metabolism parameter based on the amplitude value of the signal output by the MOS sensor, wherein the RER value is generated based on the amplitude value after compensation of the response delay of the MOS sensor, and output a result of the metabolism monitoring to the user as text or as a number.

2. The device for metabolism monitoring of claim 1, wherein the processor is further configured to:

read at least two output signals of the MOS sensor at different temperature values of a heating element and different values of relative humidity of the exhaled air, and calculate the RER value based on said read at least two output signals of the MOS sensor.

3. The device for metabolism monitoring of claim 1, wherein the device comprises at least one additional MOS sensor, and wherein the processor is further configured to:

read an output signal of the at least one additional MOS sensor placed into air flow exhaled by the user for obtaining corresponding RER values, and calculate a mean value of RER based on the obtained RER values of each of the MOS sensors.

4. The device for metabolism monitoring of claim 1, wherein the processor is further configured to:

calculate an additional metabolism parameter representing a Resting energy expenditure (REE) value, based on measured volumes of inhaled and exhaled air.

5. The device for metabolism monitoring of claim 1, wherein the processor is further configured to:

calculate an additional metabolism parameter representing fat burning rate value, based on measured volumes of inhaled and exhaled air.

6. The device for metabolism monitoring of claim 1, wherein the processor is further configured to:

calculate an additional metabolism parameter representing carb burning rate value, based on measured volumes of inhaled and exhaled air.

7. The device for metabolism monitoring of claim 1, wherein the processor is further configured to:

obtain several RER parameters during some period of time after the user has eaten food, and determine a metabolic flexibility based on the obtained RER parameters, wherein monitor adaptation of the user to changes in food ration or physical activity based on the metabolic flexibility.

8. The device for metabolism monitoring of claim 1, wherein the processor is further configured to:

obtain several RER values in a process of physical exercising of the user with controlled physical activity during some period of time, and determine an anaerobic threshold of the user based on the obtained RER values, usage of the anaerobic threshold for determining whether the user burns fats or carbohydrates.

9. The device for metabolism monitoring of claim 1, further comprising:

a pump; and a pre-concentrator for pre-accumulating the air exhaled or inhaled by the user configured to collect a portion of the air exhaled or inhaled by the user in a reservoir of the pre-concentrator, and wherein the processor is further configured to:

control the pump to pump the portion of the collected portion of the exhaled air through the device across the MOS sensor for metabolism monitoring.

10. A method for metabolism monitoring, the method comprising:

positioning a metal oxide semiconductor (MOS) sensor of a device for metabolism monitoring into an air flow path through the device for metabolism monitoring for air exhaled or inhaled by a user to output a signal corresponding to a ratio of carbon dioxide concentration in exhaled air to oxygen concentration in inhaled air;

reading the signal output by the MOS sensor by a processor of the device for metabolism monitoring;

processing the signal during successive inhalation and exhalation cycles of the user;

identifying, from the signal, a transition between inhalation and exhalation cycles;

processing the signal as a pulse of the MOS sensor for each inhalation or exhalation based on a temporal response characteristic of the MOS sensor by reconstructing rising and falling edges of the pulse of said signal;

calculating an amplitude value between a steady state of the signal of the MOS sensor after the exhalation or before the inhalation and a saturation level of the signal, wherein the amplitude value corresponds to the ratio of carbon dioxide concentration in exhaled air to oxygen concentration in inhaled air, and wherein the reconstructing of the rising and falling edges compensates for a response delay and a signal overlap between successive inhalation and exhalation cycles of the MOS sensor, wherein the reconstructing of the rising and falling edges is performed based on the temporal response characteristic of the MOS sensor and separates signals corresponding to successive inhalation and exhalation cycles, wherein the amplitude value is determined based on the signal after compensation of the response delay and signal overlap;

calculating a Respiratory Exchange Rate (RER) value representing a metabolism parameter based on the amplitude value of the signal output by the MOS sensor, wherein the RER value is generated based on the amplitude value after compensation of the response delay of the MOS sensor; and outputting a result of the metabolism monitoring to the user as text or as a number.

11. The method for metabolism monitoring of claim 10, further comprising:

reading at least two output signals of the MOS sensor at different temperature values of a heating element and different values of relative humidity of the air exhaled or inhaled by the user; and calculating the RER value based on said read at least two output signals of the MOS sensor.

12. The method for metabolism monitoring of claim 10, further comprising:

reading an output signal of at least one additional MOS sensor placed into the air flow path though the device for metabolism monitoring for the air exhaled or inhaled by the user for obtaining corresponding RER values; and calculating a mean value of RER based on the obtained RER values of each of the MOS sensors.

13. The method for metabolism monitoring of claim 10, further comprising:

calculating an additional metabolism parameter representing a resting energy expenditure (REE) value, based on measured volumes of inhaled and exhaled air.

14. The method for metabolism monitoring of claim 10, further comprising:

calculating an additional metabolism parameter representing fat burning rate value, based on measured volumes of inhaled and exhaled air.

15. The method for metabolism monitoring of claim 10, further comprising:

calculating an additional metabolism parameter representing carb burning rate value, based on measured volumes of inhaled and exhaled air.

16. The method for metabolism monitoring of claim 10, method further comprising:

obtaining several RER parameters during some period of time after the user has eaten food; and determining a metabolic flexibility based on the obtained RER parameters, wherein monitoring adaptation of the user to changes in food ration or physical activity based on the metabolic flexibility.

17. The method for metabolism monitoring of claim 10, further comprising:

obtaining several RER values in a process of physical exercising of the user with controlled physical activity during some period of time;

determining an anaerobic threshold of the user based on the obtained RER values; and using the anaerobic threshold for determining whether the user burns fats or carbohydrates.

18. The method for metabolism monitoring of claim 10, further comprising:

collecting a portion of the air exhaled or inhaled by the user in a reservoir of a pre-concentrator configured to pre-accumulate the air exhaled or inhaled by the user; and pumping the portion of the collected portion of the air exhaled or inhaled by the user through a device across the MOS sensor of for metabolism monitoring, comprising the MOS sensor.

19. The method for metabolism monitoring of claim 10, wherein a calibration curve, an equation describing that curve, or a machine learning model with coefficients which map features derived from the amplitude value of the signal output by the MOS sensor to specific RER values are used to determine the RER.

* * * * *